United States Patent
Lakrout et al.

(10) Patent No.: US 8,322,201 B2
(45) Date of Patent: Dec. 4, 2012

(54) DEVICE AND METHOD FOR ASSESSING THE MACHINABILITY OF LAMINATES

(75) Inventors: Hamed Lakrout, Midland, MI (US); Stephanie K. Anderson, Midland, MI (US); Ludovic Valette, Lake Jackson, TX (US); Nikhil Eapen Verghese, Lake Orion, MI (US)

(73) Assignee: Dow Global Technologies LLC, Midland, MI (US)

(*) Notice: Subject to any disclaimer, the term of this patent is extended or adjusted under 35 U.S.C. 154(b) by 174 days.

(21) Appl. No.: 12/811,953

(22) PCT Filed: Dec. 22, 2008

(86) PCT No.: PCT/US2008/087914
§ 371 (c)(1),
(2), (4) Date: Jul. 7, 2010

(87) PCT Pub. No.: WO2009/088723
PCT Pub. Date: Jul. 16, 2009

(65) Prior Publication Data
US 2010/0281964 A1    Nov. 11, 2010

Related U.S. Application Data

(60) Provisional application No. 61/019,856, filed on Jan. 9, 2008.

(51) Int. Cl.
*G01N 3/42* (2006.01)

(52) U.S. Cl. .......................................................... 73/82
(58) Field of Classification Search ....................... 73/82
See application file for complete search history.

(56) References Cited

U.S. PATENT DOCUMENTS

| | | | |
|---|---|---|---|
| 3,888,942 A * | 6/1975 | Tsen | 523/428 |
| 6,187,852 B1 | 2/2001 | Tungare et al. | |
| 6,447,886 B1 | 9/2002 | Mohamed et al. | |
| 6,593,255 B1 | 7/2003 | Lawton et al. | |
| 7,454,960 B2 * | 11/2008 | Ernst | 73/81 |
| 2001/0014705 A1 | 8/2001 | Tungare et al. | |
| 2005/0266756 A1 | 12/2005 | Hendricks et al. | |
| 2006/0243057 A1 * | 11/2006 | Bailey et al. | 73/788 |

FOREIGN PATENT DOCUMENTS

| | | |
|---|---|---|
| EP | 0549080 A1 | 6/1993 |
| EP | 0642919 A1 | 3/1995 |
| WO | WO-2004/109258 A1 | 12/2004 |
| WO | WO 2004109258 A1 * | 12/2004 |
| WO | WO-2005/031314 A1 | 4/2005 |
| WO | WO 2005031314 A1 * | 4/2005 |

OTHER PUBLICATIONS

Microelectronics Packaging Handbook, (1989), Tummala (Ed.) et al., pp. 896-897.

* cited by examiner

*Primary Examiner* — Lisa Caputo
*Assistant Examiner* — Jamel Williams

(57) ABSTRACT

A device and method for assessing the machinability, particularly the drillability, of epoxy resin laminates by reproducible indentation and analysis of the delamination area of a laminate sample thus provoked.

12 Claims, 6 Drawing Sheets

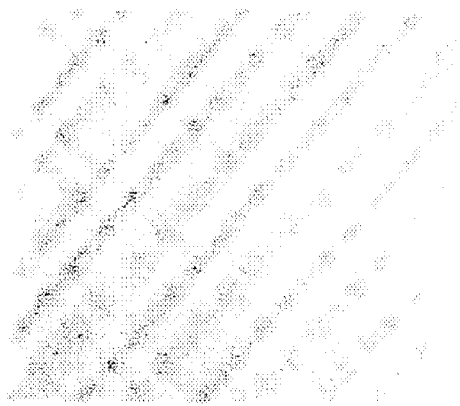

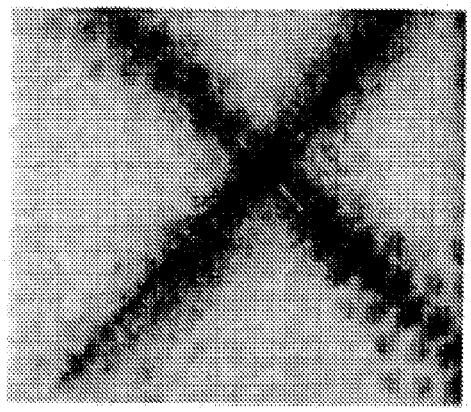

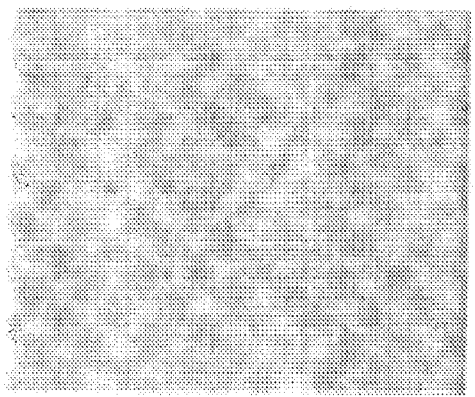

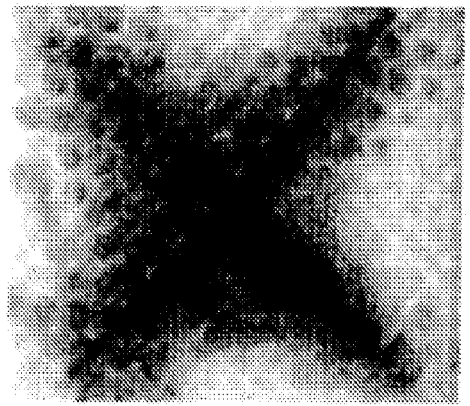

DEVICE AND METHOD FOR ASSESSING THE MACHINABILITY OF LAMINATES

FIELD OF INVENTION

The present invention relates to a device and method for assessing the machinability of epoxy resin laminates samples by reproducible indentation and analysis of the delamination area of the sample provoked by an indentation means. The present invention provides a very good correlation to actual drillability of laminate samples in a very inexpensive and quick way.

BACKGROUND OF THE INVENTION

Electrical laminates products, which are used in making printed circuit boards, typically comprise a multilayer assembly of a thermoset epoxy resin matrix in a reinforcing fiber glass mat. Printed circuit boards are typically perforated by drilling holes in the board to provide the solder connections on the board. Typically, electrical laminate products, such as those made from epoxy resins, have a high thermal resistant but are highly cross linked and display brittleness. It is therefore necessary to assess the drillability of such laminates made from various epoxy resin materials to determine if such laminates will adequately pass the rigors of the drilling step in the process of making printed circuit boards.

The performance of laminates is the result of the combination of the fracture properties of the epoxy used to make the laminate, the stiffness of the assembly and the adhesion of the epoxy matrix to the reinforcing fiber glass mat. Delamination of the layers which make up a laminate reveals a detrimental propensity of the laminate to propagate cracks when under localized pressure. There is an urgent need in the epoxy industry for a high temperature epoxy resin because of the use of such resins in lead-free soldering processes in the industry. However, a major concern is that by increasing the temperature of degradation of an epoxy, it also increases the brittleness of the epoxy. Brittleness can cause delamination and chipping of a laminate during drilling procedures. There is a need in the epoxy industry for an easy drillability testing or screening method.

Drillability of epoxy laminates is currently assessed through a costly testing process including drilling fabricated laminates using actual expensive industrial-sized laminate drilling machines. Access to such laminate manufacturer's drilling machines is not readily available. It may also take a long time to obtain such drillability results because it requires the analysis of a large number of small drilled holes on highly magnified pictures. The inaccessibility of the drilling machines makes it hard for raw material suppliers, such as epoxy resin producers, to examine the true performances of a final composite, made from a formulation of raw materials.

"Drillability" of epoxy laminates is characterized by the lifetime of a drill bit, that is, the number of hits the drill bit can survive before breakage. Another method of characterizing the "drillability" of an epoxy laminate is the wear of the drill bit over the number of hits, the wear being characterized as flankwear. These quantitative estimates are done using a laminate drilling machine.

The industry is still looking for an inexpensive way to test samples of laminates easily and quickly in order to make an efficient and a quick determination of the machinability of electrical laminates. Therefore, it is desired to provide a device and method of testing laminates. It is desired to provide a device and method for assessing the drillability of a sample of a laminate that does not require the actual drilling of the sample. It is also desired to provide a device and method that can provide a measurement of the performance of an epoxy resin from a sample of a laminate made from such epoxy resin without using a drilling tool.

It is further desired to provide a low-cost, quick method of assessing the machinability of epoxy laminates (i.e. drillability, routing, sizing and cutting) made with any epoxy resin formulation, particularly from epoxy resins having a high degradation temperature. The prior art does not teach or disclose such a low-cost quick method to screen formulations for making electrical laminates. The prior art only discloses full-scale drilling tests requiring a time-consuming trial.

SUMMARY OF THE INVENTION

The present invention is directed to a novel device and method for testing a laminate composite including producing delamination in the laminate by causing a localized deformation and rupture on the laminate using a puncher means and then examining the extent of the damage of the laminate. The larger the delamination zone on the laminate, the greater the probability for the particular resin used to make the laminate to be prone to show defects after laminate drilling procedures.

In one embodiment, the device for testing the drillability of a laminate sample includes (a) a laminate sample receiving assembly, said laminate sample receiving assembly capable of providing a sample in a disposed position for testing, and (b) an indentation means for causing an indentation on at least one surface of the laminate sample.

In another embodiment of the present invention, the device includes (a) a base; (b) a means for holding a sample, said sample holder means mounted on said base, said sample holder including a cup member for holding the sample of laminate in vertical alignment against the cup member; (c) a rod means for punching the sample perpendicular to the plane of one side of the sample causing an indentation and deformation of the sample; and (d) a means for actuating the rod means to and from the sample, said actuating means mounted on said base.

The design of the present invention device enables a low-cost assessment of the machinability (i.e. drillability, routing, sizing and cutting) of epoxy laminates. The device is used to perform reproducible indentations. A delamination area in the laminate caused by the indentation correlates with the machinability performances of the laminate. The performance of the laminate is the result of the combination of the fracture properties of the epoxy, the stiffness of the laminate assembly and the adhesion of the epoxy matrix to the reinforcing glass fibers.

The well-defined set-up of the instrument of the present invention and the use of a motor to perform the indentation leads to excellent reproducibility of the results when compared to similar but non-motorized methods.

BRIEF DESCRIPTION OF THE DRAWINGS

For the purpose of illustrating the present invention, the drawings show a form of the present invention which is presently preferred. However, it should be understood that the present invention is not limited to the precise arrangements and instrumentalities shown in the drawings.

DETAILED DESCRIPTION OF THE PREFERRED EMBODIMENTS

In the following detailed description, the specific embodiments of the present invention are described in connection with its preferred embodiments. However, to the extent that the following description is specific to a particular embodiment or a particular use of the present techniques, it is intended to be illustrative only and merely provides a concise description of the exemplary embodiments. Accordingly, the present invention is not limited to the specific embodiments described below, but rather; the present invention includes all alternatives, modifications, and equivalents falling within the true scope of the appended claims.

Unless otherwise stated, a reference to a material, a compound, or a component includes the material, compound, or component by itself, as well as in combination with other materials, compounds, or components, such as mixtures or combinations of compounds.

As used herein, the singular forms "a," "an," and "the" include the plural reference unless the context clearly dictates otherwise.

Figure 1:
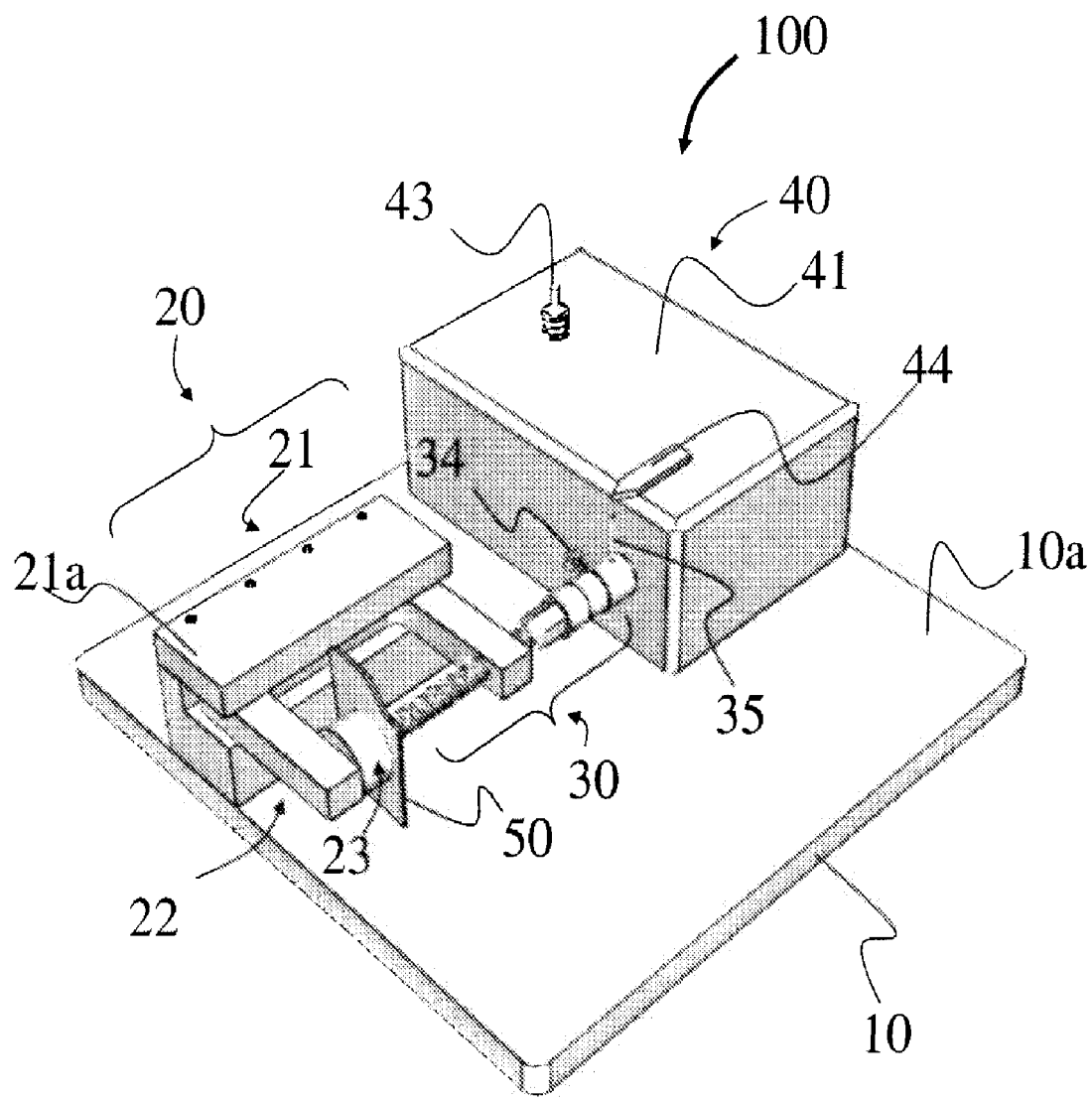
FIG. 1 is a perspective view of a device of the present invention.

Referring to the drawings wherein like numerals indicate like elements, FIG. 1 illustrates one embodiment of a screening or testing device of the present invention, which is designated generally by numeral 100. In accordance with the present invention, the testing machine or device 100 is used to test the machinability and the drillability strength of a test specimen or test sample of a laminate 50. The term "machinability" as used herein refers to the propensity of a test specimen to be cut or resized without showing cutting defects such as but not limited to burring or chipping at the edges. The term "drillability" as used herein refers to the propensity of a test specimen to be drilled without showing defects such as but not limited to delamination around the hole made by drilling or smearing around the drilled hole.

To facilitate the testing, the testing device 100 includes a sample receiving assembly which is designated generally by numeral 20 to receive the sample 50 and to hold the sample 50 in a position, and firmly in place, in preparation for subjecting the sample 50 to a pressure or punching load from a rod assembly which is designated generally by numeral 30. The rod assembly 30 is actuated by an actuating means assembly which is designated generally by numeral 40.

Figure 2:
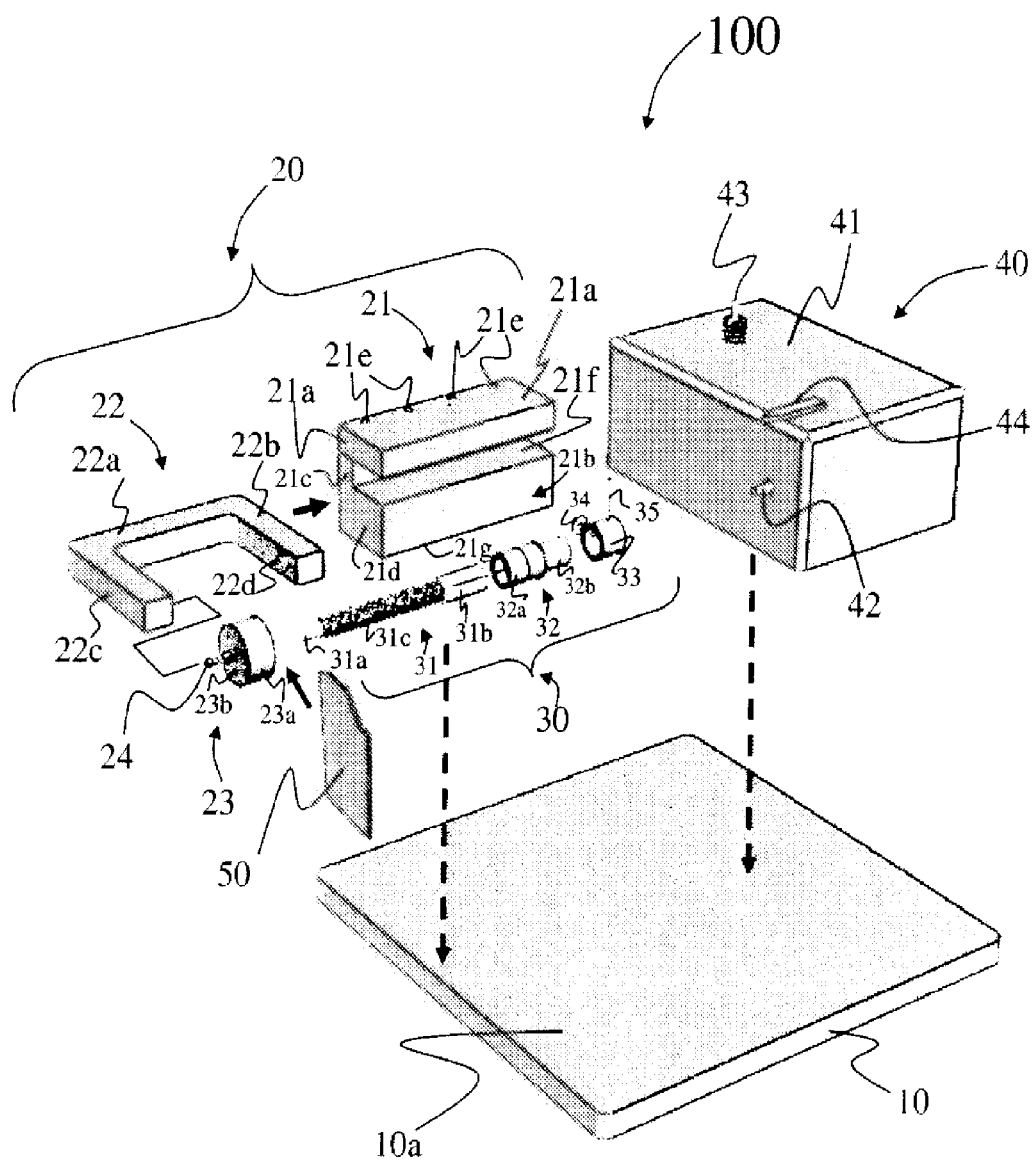
FIG. 2 is a perspective partially exploded view of a device of the present invention.
Figure 3:
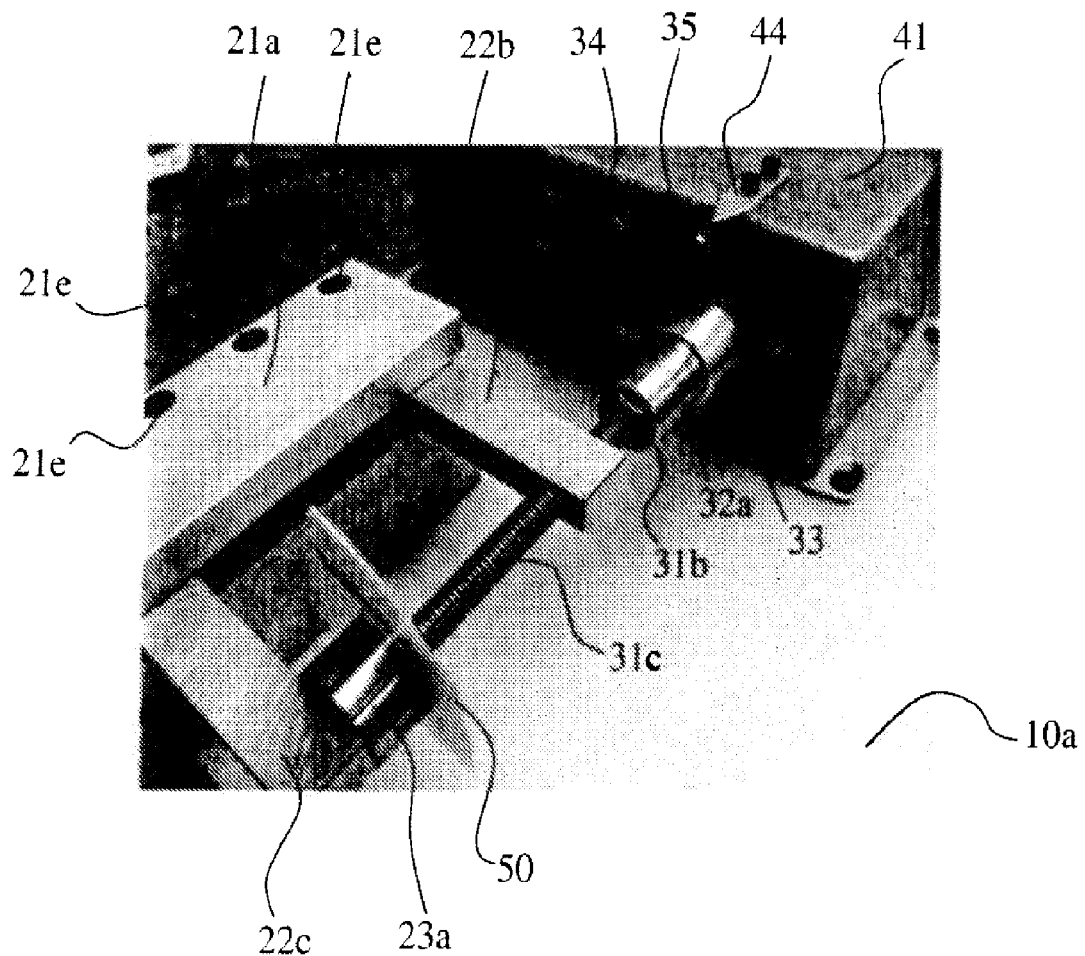
FIG. 3 is a photograph of a perspective view of a portion of a device of the present invention showing a laminate sample "pinched", i.e., held in a fixed position, between a rod member and a cup member of the device.

Referring to FIGS. 1-3, there is shown an apparatus suitable for assessing the drillability of a rectangularly-shaped (preferably square-shaped) test specimen or test sample of a fiber-reinforced epoxy resin laminate 50. The laminate sample 50 may be any geometric configuration but is preferably a flat, planar square-shaped laminate film with two sides and of a certain thickness. The sample 50 may be made of any material and can be of any thickness. Generally, a laminate is made from at least two or more layers of laminate materials; and has a typical thickness for laminates used in electronic applications. Generally, the sample 50 is made from an epoxy resin thermoset and the size of the sample for testing is generally a rectangular shape, preferably a square shape, with dimensions of from about 5 centimeters (cm) (1.97 inches) to about 20 cm (7.87 inches) in width and from about 5 cm (1.97 inches) to about 20 cm (7.87 inches) in length. Preferably, the sample is 10 cm (3.93 inches) by 10 cm (3.93 inches) square. The thickness of the sample is generally from about 0.4 millimeters (mm) (15.7 mils) to about 4 mm (157 mils), and preferably from about 1.2 mm (47 mils) to about 2.0 mm (78.7 mils). The sample is subjected to a means for applying a variable indentation load thereto to cause the sample to be deformed but not a load sufficient to tear or puncture the sample through its thickness.

In its most simplest form, the apparatus 100 of the present invention comprises a base 10; a sample receiving assembly generally indicated by numeral 20 capable of receiving a sample 50 for testing; an indentation or punching rod assembly generally indicated by numeral 30 capable of contacting and deforming the sample 50; and an actuating means generally indicated by numeral 40 capable of actuating the punching rod assembly 30 toward and against the sample 50, and also capable of moving the punching rod assembly 30 away from the sample 50. The materials of construction for the components of the apparatus 100 of the present invention may be of any material sufficient to provide the testing loads to the sample 50. For example, the components of the apparatus 100 of the present invention may be formed of steel or a similar metal.

The base or platform 10 is the foundation for mounting the other components of the apparatus 100. Generally, the base 10 is a rectangular platform of any size and thickness. In one embodiment, the base 10 may be about 12 inches (30.5 cm) by about 12 inches (30.5 cm) square and about ¼ inch (6.35 mm) thick. The platform 10 may be of any material of construction, for example, the material may typically be polyethylene, polypropylene, wood, steel, etc. The base 10 with the other components of the device 100 attached thereto is portable which makes the device 100 useful for laboratory tables or desktops.

The sample receiving assembly 20 is suitably anything that can receive a sample 50, wherein the sample 50 can be placed or disposed in a position for testing. In a preferred embodiment, the sample receiving assembly 20 comprises an elongated U-shaped channel member generally indicated by numeral 21; a U-shaped bracket member generally indicated by numeral 22 slidably mounted to the U-shaped channel member 21; and a cylindrical cup member generally indicated by numeral 23 attached to the U-shaped bracket member 22. The cylindrical cup member 23 may be attached to or affixed to the U-shaped bracket member 22 by any suitable attachment means, for example, using an adhesive, a clamping means or a screw means. In this instance, the cup member 23 is attached to one arm 22c of the U-shaped bracket member 22 with a screw member 24 and a threaded cavity (not shown) on one side of the arm 22c to receive the screw member 24.

The indentation rod assembly, also referred to herein interchangeably as a punching rod assembly, 30, comprises an elongated threaded rod member generally indicated by numeral 31; a cylindrical adaptor member generally indicated by numeral 32; a cylindrical collar member 33; a tightening screw means 34; and an indicator pin 35. The punching rod assembly 30 is coupled to the actuating means assembly 40 via a shaft member 42.

The actuating means assembly 40 includes for example one or more motors (not shown) or other devices that provide the ability to move and control the punching rod assembly 30. The motor or motion means is preferably housed in a housing 41. The motor in the housing 41 provides a means for rotating a rotational transfer means, represented by rotable shaft member 42. The rotable shaft member 42 is connected to the motor on one end and connected to the punching rod assembly 30 on the opposite end; and the shaft member 42 transfers rotational motion to the punching rod assembly 30. The actuating means assembly 40 further comprises an off-on switch member 43 to turn the motor off or on, and an indicating means 44 attached to the housing 41.

The sample receiving assembly 20 and the actuating means assembly 40 are preferably attached to or mounted on the base 10. The attachment of components 20 and 40 can be made with any known means such as with an adhesive; with clamps; with nuts and bolts; or with screw means.

In one embodiment, the U-shaped channel member 21 of the sample receiving assembly 20, comprises a removable rectangular block member 21a removably attached to an L-shaped member, depending on its view, generally indicated by numeral 21b, forming a U-shaped channel or C-shaped channel when the block member 21a and the L-shaped member 21b are assembled together. Member 21b is L-shaped when viewed in cross-section; and has a portion 21c which forms the base of the "U" of the U-shaped member 21, and a portion 21d which forms one of the arms of the "U" of the U-shaped member 21. The block member 21a forms the other arm of the "U" of the U-shaped member 21. The removable member 21a can be removably attached to the L-shaped member 21b by any known means such as an adhesive, a screw means, or nuts and bolts. In this instance the member 21a is attached to member 21b by a plurality of threaded bolts 21e as shown in FIG. 2. The removable member 21a of the U-shaped channel member 21 provides a means to facilitate disassembly of the apparatus and to guide the horizontal sliding motion of the U-shaped bracket number 22 during the indentation; of the laminate sample by the punching rod assembly 30; and provides a means to easily handle the sample 50 once the sample is clamped between the cup means 23 and the indentation rod assembly 30. Alternatively, the U-shaped channel member 21 can also be machined as a one-piece member instead of the individual pieces 21a and 21b.

When the block member 21a and the L-shaped member 21b are assembled integrally together with threaded bolts 21e, the resultant U-shaped channel member 21 preferably has a base portion 21c; and one arm 21a and another arm 21d (as shown in FIG. 2), respectively. The U-shaped channel member 21 forms a groove or channel 21f for receiving U-shaped bracket member 22. The U-shaped bracket member 22 is slidably mounted in U-shaped channel member 21 through the channel 21f. The sample receiving assembly 20 is attached or mounted to the base 10 via the L-shaped member 21b by attaching the bottom surface 21g of the L-shaped member 21b to the top surface face 10a of the base member 10. The U-shaped channel member 21 is mounted on the base 10 such that the groove or channel 21f of the U-shaped channel member 21 is aligned horizontally and parallel to the face 10a of the base 10.

The U-shaped bracket member 22 of the sample receiving assembly 20, comprises a base portion 22a integral with two arm portions 22b and 22c, respectively. The arms 22b and 22c are spaced apart from each other, are parallel to each other; and are integral with the base 22a to form a U-shaped member. The arms 22b and 22c are perpendicular to the base 22a on one side of the base to form the U-shaped (or C-shaped member depending on its view) bracket member 22. The U-shaped bracket member 22 is aligned with the base portion 22a of member 22 being slidably mounted to the channel 21f of U-shaped channel member 21 with the arms 22b and 22c protruding perpendicular from the channel 21f of the U-shaped channel member 21; and the arms 22b and 22c are horizontally and parallel to the face 10a of the base 10.

One arm 22b of the U-shaped bracket member 22 contains a threaded hole 22d for receiving the threaded rod member 31. The cup member 23 is attached to the inside surface of the second arm member 22c wherein the cup mouth 23c (shown in FIGS. 5A and 5B) of the cup member 23 is positioned such that the cup mouth 23c faces directly across from the threaded hole 22d located on the opposite arm 22b. The cup mouth 23c of the cup member 23 is disposed on arm member 22c such that the threaded rod member 31 travels perpendicular to the plane of the cup mouth 23c. The cylindrical cup member 23 may be attached to the arm 22c by any known means such as by adhesion, screw means, or nuts and bolts. In this instance, the cylindrical cup member 23 is attached to the arm 22c via a screw member 24.

The cylindrical cup member 23 of the sample receiving assembly 20, comprises a cylindrical wall 23a integral with a circular base 23b forming a cylindrical cavity or mouth 23c of the cylindrical cup member 23. The base portion 23b of the cup member is attached to arm 22c via a screw means 24 with the outside bottom surface 23d of the cup member contacting the inside surface of arm 22c. If desired the cup member 23 may be any geometry other than cylindrical.

The threaded rod 31 of the punching rod assembly 30 has a distal end portion 31a and a proximal end portion 31b with a threaded middle portion 31c between the distal and proximal ends. The distal end portion 31a has a smooth hemi-sphere shaped head or tip portion 31a which is used to contact the sample 50. The proximal end portion 31b has a hexagonal sided male portion 31b used to couple the threaded rod 31 to an adaptor member 32.

The adaptor member 32 comprises a cylindrical member having a hexagonal sided socket female portion 32a at one end for receiving the hexagonal sided male portion 31b of the threaded rod 31 and a rectangular or square sided socket female portion 32b at the other end of the adaptor member 32 for receiving the shaft member 42 of the actuating means assembly 40. The adaptor member 32 has one end for connecting the adaptor member 32 to the rod member 31 and another end for connecting to adaptor member 32 to the rod member 42 protruding from the housing 41 of the actuating means 40.

The proximal end portion 31b of the threaded rod 31 may be any geometry suitable for coupling to the socket female portion 32a of the adaptor member 32. The hexagonal socket female portion 32a of the adaptor member 32 may be any shape or geometry for receiving the corresponding geometry of the proximal end portion 31b of the threaded rod member 31. In addition, the rectangular socket female portion 32b of the adaptor member 32 may be any shape or geometry for receiving the corresponding geometry of the shaft member 42 of the actuating means assembly 40. The cylindrical adaptor member 32 is adapted for inserting into and connecting to a cylindrical collar member 33.

The collar member 33 is a component of the punching rod assembly 30 that is removably attached to the outer cylindrical surface of portion 32b of the adaptor member 32. The collar member 33 contains a removable set screw member 34 used to affix the collar member 33 to the outer cylindrical surface of portion 32b of the adaptor member 32. An indicator pin 35 is attached perpendicular to the outer cylindrical surface of collar 33 to provide a visual indication of the number of turns or rotations the rod member 31 of the punching rod assembly 30 moves during the testing.

The actuating means 40 comprising a motor (not shown) which is in rotable connection with shaft member 42 for rotating the shaft member 42 and the punching rod assembly 30. The motor and shaft member 42 are housed with housing 41. A switch 43 on the housing 41 is used to turn the motor "on" or "off". In a preferred embodiment, the switch 43 is spring-loaded to turn the motor "off" if not actuated (pushed) by a user, i.e., the switch is constantly "on" while being actuated by the finger of a user, but once the finger is removed from the switch, the switch automatically springs back to an "off" position. An indicating means 44 is attached on the housing 41, preferably on the top surface of the housing and slightly protruding from the housing surface; and the indicating means 44 is aligned above the punching rod assembly 30 and perpendicular to the indicating pin 35. The indicating means 44 and indicator pin 35 provide a visual measurement of the number of turns the punching rod assembly 30 takes during testing.

In its simplest form, the method of testing a sample includes providing a sample 50 in a fixed positioned such that an indentation on one side or surface of the sample can be made using the apparatus 100 of the present invention.

Figure 4:
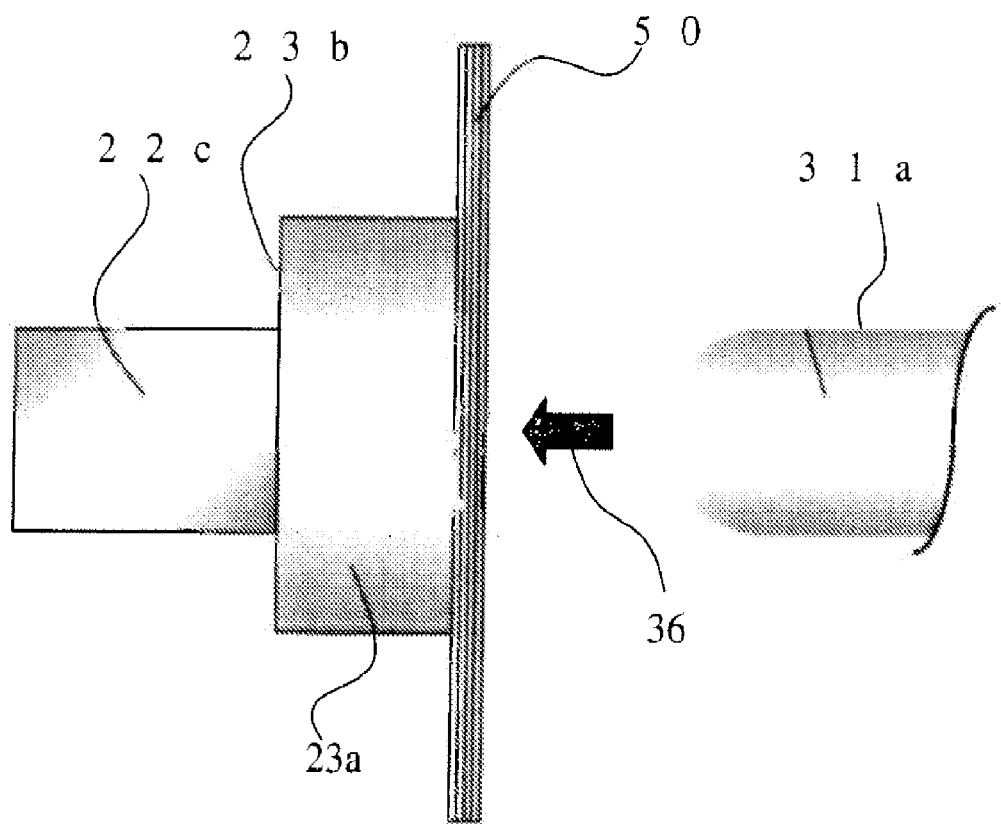
FIG. 4 is a side view of a cup member and a rod member of a device of the present invention including a sample attached to the cup member before the sample is deformed by pressing a head portion of a rod member against the sample.
Figure 5A:
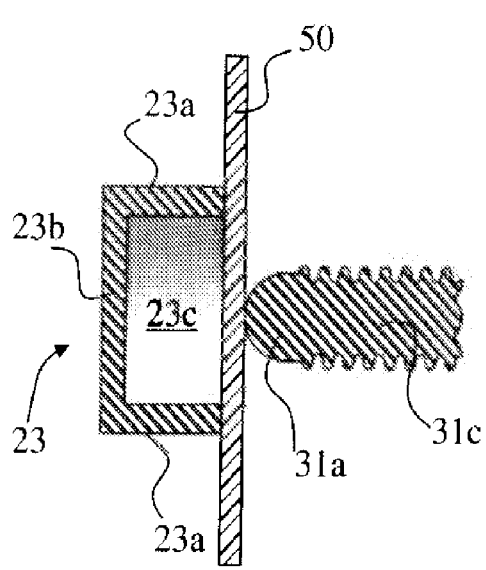
FIG. 5A is a cross-sectional view of a laminate sample "pinched," i.e., held in place, between a cup member and a head portion of a rod member of the device of the present invention just before the sample is deformed.
Figure 5B:
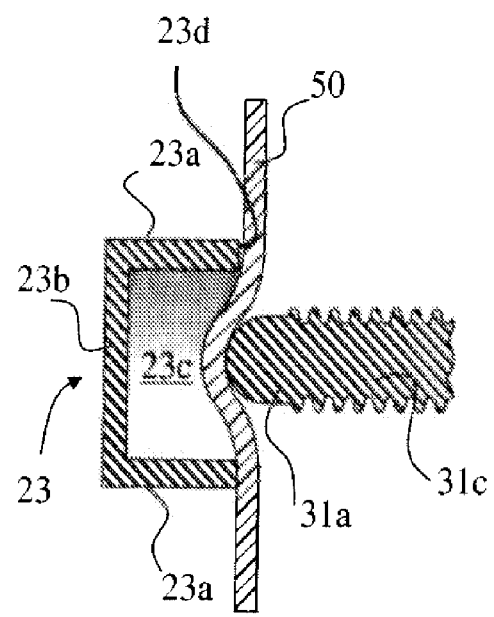
FIG. 5B is a cross-sectional view of a laminate sample with a pressing load bearing against the laminate sample shown in FIG. 5A between the cup member and the head portion of the rod member of the device of the present invention showing a predetermined amount of indentation or deformation of the laminate sample.

With reference to FIGS. 4, 5A and 5B, there is shown a laminate sample 50 before being tested (FIGS. 4 and 5A) and after the sample 50 is tested (FIG. 5B). As previously described above with reference to FIGS. 1-3, the sample receiving assembly 20 includes a cylindrical cup member 23 and a rod assembly 30 having a threaded rod member 31. The sample of laminate 50 to be tested is held in vertical alignment between the cup member 23 and the rod member 31 such that the rod member 31 punches the sample 50 perpendicular to the sample causing deformation of the sample. The deformation of the sample takes the form of, for example, an indentation which causes delamination of the multilayers which make up the sample. The materials of construction of the apparatus 100 may be of any material sufficient to provide the testing loads to the sample 50. Preferably the apparatus 100 is formed of steel or other metal.

The wall 23a of the cylindrical cup member 23 contains cup mouth 23c with a lip or rim 23d for supporting one side, i.e. the back side, of the test specimen 50. Normally, the test specimen 50 will be approximately 2 inches (5.08 cm) wide by 2 inches (5.08 cm) long, and the cup member 23 should be sized accordingly. For example, the circular cup mouth 23c of the cylindrical cup member 23 is generally about 1 inch (2.54 cm) in diameter. The punching load is applied to the test specimen 50 by means of the rod assembly 30 wherein the head portion 31a rests on the other side, i.e. the front side, of the test specimen 50 while the back side of the specimen 50 rests on the rim 23d of the cup mouth 23c of the cup member 23. The threaded portion 31c of the rod member 31 threads through a threaded opening 22d in the arm 22b of the U-shaped bracket member 22; and the punching strain (deformation) imposed on the test specimen 50 is controlled by the actuating means 40 by observing the number of rotations or turns made by the pin member 35 and the final position of the pin member 35. The base 10 provides a platform and foundation to secure the actuating means 40 and sample receiving assembly 20 to prevent the apparatus from moving out of alignment during a test procedure.

To carry out the process of testing a sample, the sample is placed centered on the cup mouth 23c of the cup member 23 to cover the cup mouth 23c of the cup member 23. The sample 50 may be tacked onto the rim 23d of the cup mouth 23c of the cup member 23, for example, with tape or an adhesive to hold the sample 50 in place as shown in FIG. 4 until contact is made against the sample by the rod assembly 30. Alternatively, as shown in FIG. 5A, the sample 50 may be first suspended between the cup member 23 and the rod assembly 30 by a user of the device; and then the rod member 31 rotated manually until slight contact is made by the rod member 31 against the front surface of the sample 50 by a very light pressure sufficient only to hold the sample in place until testing begins. At this point, the sample 50 is disposed between the cup 23 and the head portion 31a of rod member 31 as shown in FIG. 5A; and as shown in FIGS. 1 and 3.

To start the testing process, the motor is turned on by the switch 43. The motor begins turning the shaft 42 connected to the motor, which in turn, rotates the rod assembly 30. The threaded rod 31 is positioned at the entrance of the threaded hole 22d of the arm 22b of the U-shaped bracket member 22 so as the rod member 31 is rotated the threaded portion 31c of the rod member 31 bores through the threaded hole 22d in a rotating action, which in turn, moves the U-shaped bracket member 22 along the channel 21f in a sliding movement toward the proximal end portion of the rod 31, i.e., in the opposite direction of the rod member 31. As the U-shaped bracket member 22 moves horizontally sliding through the groove 21f and moves in a direction horizontally and parallel to the face 10a of the base 10 toward the proximal end portion of the rod member 31, the cup member 23 and sample 50 on the arm 22c moves toward the distal end head portion 31a of the rod member 31. The distal end 31a moves in the direction of the arrow indicated by numeral 36 as shown in FIG. 4. This creates a punching action against the front side or face of the sample 50, which in turn, causes deformation or damage to the sample 50. A predetermined pressure or load is placed against the sample, sufficient to deform the sample 50 but not enough to puncture or tear the sample, particularly not tearing or penetrating completely through the thickness of the sample 50.

At the start of the test, the indicator pin 35 is positioned across from the indicator member 44 attached to the housing 41. A predetermined number of complete rotations or part rotations are recorded by the user of the device 100 after visually observing the number of turns of the indicator pin 35 takes to where the pin stops. The number of revolutions or turns correlates to a predetermined load or pressure on the sample. The number of turns may also be correlated to a predetermined distance the head portion 31a of the rod member 31 travels into the surface of the sample 50 without puncturing the sample as shown in FIG. 5B. The resulting permanent deformation of the sample 50, in turn, corresponds to the machinability or drillability of the sample 50 based on comparisons to other standard samples having acceptable machinability and drillability.

In the present embodiment, the pressing of a load against the sample or "punching" of the sample is controlled manually by manually activating the on-off switch 43 of the apparatus of the present invention. In other embodiments of the present invention, the on-off switch, control of revolutions of the rod member 31 of the apparatus, and control of the actuation movement can all be exercised using computerized or other automated equipment. The amount of pressure or load applied to the sample and the depth of the punch delivered to the sample is reproducible. A reproducible punch is achievable by moving the punching rod assembly in a predetermined speed and distance against a sample. Such speed and depth can be set on a variety of computerized (including chip-controlled or other programmable means) or similarly controlled equipment. In a preferred embodiment, the depth or severity of the punching may be adjustable by using an adjustment means (not shown) to control distance between the sample cup and the rod member 31. While this distance is manually controllable, simplicity and reproducibility favor automated control.

Once the rod member 31 has been actuated against the sample 50 and the desired indentation has been made to the sample, the actuating means is stopped. At this point, the U-shaped bracket member 22 is holding the cup member 23, the sample 50 and the threaded rod 31 of the rod assembly 30, because the sample 50 is "pinched" between the cup member 23 and the threaded rod 31. At this point, a user may disengage from the actuating means 40, the U-shaped bracket member 22 along with the cup member 23, the sample 50 and the threaded rod member 31, by sliding the hexagonal male portion 31b of the threaded rod 31 away from the hexagonal sided socket female portion 32a of the adaptor 32 through the channel 21f of the U-shaped channel member 21 in the opposite direction from the actuating means 40. A user of apparatus 100 may then quickly disassemble the sample 50 from the sample receiving assembly 20 by manually backing up the threaded rod member 31, so that the sample 50 is released from the "pinched" position; and then the sample 50 may be analyzed rapidly. In other words, in order to remove the sample 50 from the sample receiving assembly 20, the rod assembly 30 is simply actuated in reverse to back the threaded rod member 31c away from the sample 50; and then the sample 50 is disattached from the cup member 23 for further analysis.

In another embodiment, the removable rectangular member 21a of the U-shaped channel member 21 may be disattached from the U-shaped channel member 21 by removing the threaded bolt members 21e. This may allow a user to have an easier access to the punching rod assembly 30 and to more easily disengage the threaded rod 31 from the adaptor 32 by sliding away the hexagonal male portion 31b of the rod 31 from the hexagonal female socket portion 32a of the adaptor 32.

The removablility of the components comprising the U-shaped bracket member 22, the cup member 23, the sample 50 and the threaded rod member 31, allows for the portability of the U-shaped bracket 22 containing the sample 50; and contributes to the ease of disassembling the apparatus 100.

After a sample is punched or indented using the apparatus of the present invention, the indentations are suitably evaluated by any means within the skill in the art, depending on the purpose of studying the indentations. For instance, microscopic examination and imaging are among appropriate ways to evaluate the nature of indentations. Comparative evaluations preferably involve some reproducible measurement such as measurements of physical properties changed by indentation such as overall aspect or color of the test specimen or a combination thereof. The device of the present invention advantageously provides a sufficiently large pattern of damage or deformation on the surface of a sample that the change in surface configuration can be quantified using the diagonal size of the cross pattern appearing because of the indentation and causing a whitening visible at the naked eyed. Standard methods of measuring such properties include, for example, optical microscopy and stereo microscopy, and analysis of pictures of the test specimen to measure the size of the cross in its diagonal dimension. Comparison of these differences on laminate samples of different composition shows differences in indentations. Such measurements can be made quickly and reproducibly, for instance using a low magnification microscope.

Particular types resins used to make laminates can be studied using the device of the present invention. It is found, for instance, that the density of the damage pattern controlled by the depth of the indentation correlates with the severity of the damage by drilling to a sample observed in manufacturing.

Figure 6A:
FIG. 6A is a photomicrograph of a laminate sample prior to being deformed using a device and method of the present invention.
Figure 6B:
FIG. 6B is a photomicrograph of the laminate sample shown in FIG. 6A, after being subjected to testing using the device and method of the present invention, showing good and acceptable machinability characteristics.

In FIG. 6A there is shown a test sample of a laminate known to have good machinability properties and known to be able to be drillable. FIG. 6B shows the same test sample of FIG. 6A after the sample has been tested with the apparatus of the present invention. FIG. 6B shows a certain amount of permanent deformation to the sample in the shape of a white cross-shaped feature, but not a significant amount of permanent deformation to classify the sample as being unacceptable for drilling.

Figure 7A:
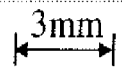
FIG. 7A is a photomicrograph of a laminate sample prior to being deformed using a device and method of the present invention.
Figure 7B:
FIG. 7B is a photomicrograph of the laminate sample shown in FIG. 7A, after being subjected to testing using the device and method of the present invention, showing unacceptable machinability characteristics.

In FIG. 7A there is shown a test sample of a laminate, with unknown machinability properties, before the sample is tested. FIG. 7B shows the same sample of FIG. 7A after the sample has been tested with the apparatus of the present invention. FIG. 7B shows a significant amount of permanent deformation to the sample which classifies this sample as being unacceptable for drilling.

There are other variations of the device of the present invention, including for instance, wherein the cup means of the sample receiving assembly may be sized to accommodate larger, smaller, thinner or thicker samples, and in the punching rod assembly is of a size of an appropriate material and a load to punch different materials and of any material whose indentation behavior is of interest. Such variations are within the skill in the art. Optionally, the punching rod assembly may include at least one load measuring device, at least a depth gauge device, or a combination thereof. A load measuring device records the normal force applied on the rod assembly. A measuring device is optionally and preferably connected to a, preferably high speed, automatic data acquisition system.

Within the scope of the present invention, one physical part may serve the function of two or more illustrated items. For example, the threaded rod 31, the adaptor 32 and collar 33 can be one piece that serves the functions of connecting to the transfer means (shaft 42) and delivering a punching load to the sample 50.

The actuating means that provides rotational movement to the shaft 42 is optionally a series of parts, for instance a series of gears, pulleys, shafts, or a combination thereof could be used to translate rotational motion to the shaft 42 and rotating means to the rod assembly 30 and perpendicular to the sample 50. The sample receiving assembly 20 in most instances is more than one piece, having one or more parts for support, one or more parts for clamping and one or more parts for movement of the sample perpendicular against the rod assembly 30. Likewise, two or more physical parts may combine to serve a purpose illustrated by one piece in the Figures. For instance, sample receiving assembly and punching rod assembly could be a series of apparatus parts that serve the ultimate function of translating motion from a source of motion to the punching means. Likewise, it is not necessary that there be one motion in a precise or exactly perpendicular angle (90 degrees), other angles can be used if desired as long as the punching rod assembly sufficiently contacts the sample to provide a useful indentation without tearing the sample so much that measurement is less meaningful. It is also within the scope of the invention for the parts to be arranged differently. For instance, the sample receiving assembly and the punching rod assembly is shown in the Figures as being parallel to the base with the rotating of the rod assembly being in some position sharing an axis of rotation. Optionally, the parts may be in a vertical position perpendicular to the base, floor or bench.

The following examples illustrate, but do not limit the present invention. All parts and percentages are based upon weight, unless otherwise specified.

EXAMPLE 1

A 2 inches (5.08 cm) by 2 inches (5.08 cm) square and ¼ inch (6.35 mm) thick sample of a multilayer laminate made from an epoxy resin product D.E.R.* 592-A80 (Trademark of The Dow Chemical Company), cured with dicyandiamide and catalyzed with 2-methyl imidazole, was tested in the device of the present invention in accordance with the following testing method: The test specimen was placed in the device of the present invention and the switch of the apparatus was held in the "on" position until the indicator pin made 2 rotations.

FIG. 6A is a photomicrograph of the laminate sample without any deformation just prior to subjecting the sample to a pressure load from the rod member of the device of the present invention. FIG. 6B is a photomicrograph of the laminate sample of FIG. 6A after subjecting the sample to a pressure load from the rod member of the device of the present invention. As shown in FIG. 6B, there is a uniform permanent deformation in the shape of an "X" in the center of the sample. The size of this deformation is correlated to the fact that the sample can be drilled. The relatively small sample deformation indicates that the sample is acceptable to drillability.

EXAMPLE 2

A 2 inches (50.8 cm) by 2 inches (50.8 cm) square and ¼ inch (6.35 mm) thick sample of a multilayer laminate made from an epoxy resin product XU 19074.00, cured with XZ92535.00, two commercial resins of The Dow Chemical Company, and catalyzed with 2-methyl imidazole, was tested in the device of the present invention according to the same procedure as described in Example 1.

FIG. 7A is a photomicrograph of the laminate sample without any deformation just prior to subjecting the sample to a pressure load from the rod member of the device of the present invention. FIG. 7B is a photomicrograph of the laminate sample of FIG. 7A after subjecting the sample to a pressure load from the rod member of the device of the present invention. As shown in FIG. 7B, there is a non-uniform permanent deformation in the shape of an "X" with random damage extending beyond the center of the sample. The size of this is deformation is correlated to the fact that the sample can not be drilled. The large extent of the sample deformation indicates that the sample is unacceptable to drillability.

While the present invention has been described and illustrated by reference to particular embodiments, those of ordinary skill in the art will appreciate that the present invention lends itself to variations not necessarily illustrated herein. For example, as aforementioned, the device can be arranged such that the sample 50 is disposed horizontally and parallel to the surface 10a of the base 10 and the indention means is arranged such that the indention pressure is applied vertically and perpendicular with reference to the plane of the sample 50. For this reason, then, reference should be made solely to the appended claims for purposes of determining the true scope of the present invention.

What is claimed is:

1. A device for testing the machinability and/or the drillability of a laminate sample comprising (a) a laminate sample receiving assembly including a cup member having a mouth, and wherein the laminate sample is positioned in vertical alignment on the plane of the mouth of the cup member, said laminate sample receiving assembly capable of providing a laminate sample in a disposed position for testing, and (b) an indentation means for causing an indentation on at least one surface of the laminate sample, wherein the laminate sample is vertically disposed in the sample receiving assembly and perpendicularly disposed to the indentation means.

2. The device of claim 1 wherein the indention means includes a rod member and a rod actuating means for actuating the rod means toward and away from the sample in a perpendicular direction in relation to the vertical plane of the surface of the sample, said rod member capable of providing a load against the laminate sample perpendicular to the vertical plane of the sample causing deformation of the sample.

3. The device of claim 1 wherein the laminate sample receiving assembly and the indentation means are mounted on a base member so that the device is made portable.

4. The device of claim 2 wherein the rod member has a distal end and a proximal end, wherein the distal end presses against the sample; and wherein the proximal end is affixed to the rod actuating means.

5. The device of claim 1 wherein the cup member is cylindrical in shape and has a cylindrical wall integral with a circular base forming an opened cup mouth circular in shape.

6. The device of claim 2 wherein the indentation means includes a U-shaped bracket member and a U-shaped channel member; and wherein the rod member is a threaded rod member and is threadably connected through a threaded hole in one arm of a U-shaped bracket member; and wherein the U-shaped bracket member is slidably mounted to the U-shaped channel member.

7. The device of claim 1 wherein the distal end of the rod member which presses against the sample is hemi-sphere in shape.

8. The device of claim 1 wherein the wherein the circular mouth of the cup member is from about 1 inch (2.54 cm) to about 1.5 inches (3.81 cm) in diameter.

9. A process for testing the machinability and/or the drillability of a film or laminate sample comprising the steps of (a) providing a laminate sample receiving assembly, said laminate sample receiving assembly capable of providing a laminate sample in a disposed position for testing, (b) providing an indentation means having a punching rod assembly for causing an indentation on at least one surface of the laminate sample, (c) providing a sample in the laminate sample receiving assembly, (d) contacting the sample with the punching rod assembly such that an indentation is formed in the sample, and
(e) evaluating the indentation on the sample to determine the effects of indenting the sample.

10. The process of claim 9 wherein indentation produced on the sample is reproducible and of a size sufficient to be analyzed using visual observation means.

11. The process of claim 9 wherein the indentation on the sample is correlated to drillability characteristics of a like sample.

12. A method for assessing the machinability of a film or a laminate sample comprising the steps of:
(a) affixing a film or a laminate test sample to a sample receiving means to provide the sample in a disposed position to be punched with an indentation means,
(b) punching the sample with the indentation means to a create an indentation in the sample, said indentation means moving substantially perpendicular to the plane of the sample, said indentation moving a sufficient distance into the sample such that the indentation means provides a sufficient indentation but does not puncture the sample completely through the thickness of the sample, and
(c) visually measuring the indentation by comparing the indentation on the test sample to a standard sample before and after punching the test sample.

* * * * *